United States Patent [19]

Reichard

[11] Patent Number: 4,538,451
[45] Date of Patent: Sep. 3, 1985

[54] MACHINE FOR DETECTING SUGAR CRYSTALS IN MOLASSES

[75] Inventor: Stefan R. Reichard, Mackay, Australia

[73] Assignee: Sugar Research Limited, Queensland, Australia

[21] Appl. No.: 587,963

[22] Filed: Mar. 9, 1984

[51] Int. Cl.³ .................................. G01N 15/00
[52] U.S. Cl. ............................. 73/61 R; 127/9
[58] Field of Search ........... 127/2, 9; 73/61 R, 61.1 R

[56] References Cited

U.S. PATENT DOCUMENTS

| | | | |
|---|---|---|---|
| 3,269,172 | 8/1966 | McGaughey | 73/61 R |
| 3,822,582 | 7/1974 | Etkin | 73/61 R |
| 3,837,216 | 9/1974 | Shinohara | 73/61 R |
| 3,906,780 | 9/1975 | Baldwin | 73/61 R |
| 4,240,287 | 12/1980 | Mast et al. | 73/61 R |
| 4,450,712 | 5/1984 | Shaughnessy | 73/61 R |

*Primary Examiner*—Kenneth M. Schor
*Attorney, Agent, or Firm*—Stevens, Davis, Miller & Mosher

[57] ABSTRACT

There is disclosed apparatus for detecting solids in a fluid. A method of detecting solids in a fluid is also disclosed. The apparatus includes fluid sampling means within a housing. The sampling means conveys a sample of the fluid to a testing station adjacent which a movement or vibration detector is mounted. The flow path of the sample is restricted to crush or tend to crush solids in the fluid and cause movement or vibrations detected by the detector and means for providing a visual and/or audible output indicate the presence of solids in the fluid.

9 Claims, 8 Drawing Figures

TYPICAL CHART RECORDINGS OF CRYSTAL DETECTION.

MACHINE FOR DETECTING SUGAR CRYSTALS IN MOLASSES

The invention relates to a device for detecting solid particles in a fluid and to a method of detecting solid particles in a fluid. In particular, the invention concerns a device for and method of detecting sugar crystals in molasses. The invention will be described by way of example in relation to this particular application but it should be appreciated that this is by way of example only and that the invention may be used for other applications.

The screens in continuous centrifugals used for separating sugar crystals from molasses can become damaged and thus allow sugar to escape into the molasses. If the damage is small it can remain unnoticed for some time and the loss of sugar can be significant. This problem has been known for some time and visual methods of detecting crystals in molasses have evolved but these methods are not satisfactory. Ultrasonic and radio frequency methods of solid particle detection have been tried and have proven ineffective.

It is an object of the present invention to provide a device for and a method of detecting solid particles in a fluid which enables automatic detection of the presence of solids in a fluid which at least minimises the disadvantages of prior methods and apparatus mentioned above.

According to one aspect, the invention provides a device for detecting the presence of solids in a fluid including a housing having an inlet for fluid and an outlet for fluid;

fluid sampling means within the housing for directing a sample of the fluid to a testing station within the housing;

detection means adjacent the testing station;

means for restricting the path through the testing station whereby the fluid sample is caused to flow through the testing station and any solid particles in the fluid are crushed or tend to be crushed causing movement or vibrations which may be detected by the detection means; and output means coupled to said detection means for providing a visual and/or audible indication of solid particles in the fluid.

According to another aspect of the invention there is provided a method of detecting the presence of solid particles in a fluid, comprising obtaining a sample of fluid from a fluid stream, conveying the fluid sample to a testing station and restricting the flow of the sample through the testing station to thereby crush or tend to crush any solid particles present in the sample, detecting movement or vibrations caused by the passage of the solid particles through the testing station and providing an output indicative of the number of solid particles crushed or tending to be crushed as the fluid moves through the testing station.

In a preferred form of the invention, mounting means are present for securing the detection means relative to the housing. Preferably the mounting means enables the detection means to project into the housing through an opening adjacent the testing station. The mounting means may be adjustably secured to the housing to enable the degree of restriction of the fluid through the testing station to be altered. The mounting means may comprise a plate secured to the housing in such a manner to enable the spacing between the plate and the sampling means to be selectively altered. The mounting means may comprise an anvil bar secured to the housing. The anvil bar may be secured to the interior of the housing and adjacent the opening in the housing mentioned above. The detection means may be secured to the anvil bar so as to project into the housing through the opening.

The anvil bar may be made adjustable in any suitable manner. Preferably, one end of the bar is secured to the inside of the housing so that the other end of the bar may be moved away from the housing and towards the sampling means. In this way the detection means, which is mounted intermediate the ends of the bar, may be moved towards the sampling means. In one embodiment, the end of the bar is welded to an inside surface of the housing and the other end may be moved away from that surface by a set screw threaded through the housing adjacent the other end of the bar.

The detection means is preferably a movement, vibration or shockwave sensitive detector. Vibrations caused by crushing of the solid particles may be detected using one of several types of sensors. For example, a passive ultrasonic transducer or strain gauge or accelerometer could be employed. This list of possible sensors is not exhaustive and other types may equally be used.

The detection means may be mounted relative to the housing in any suitable fashion.

If an accelerometer having a threaded stud is used, this stud may be threaded into a correspondingly threaded hole in the bar or boss or the like, provided on the bar. The output from the detection means may be fed to the signal processing means and output means in any suitable fashion. For example, a cable such as coaxial or shielded cable may be used for this purpose.

The signal processing means may include amplifying means for increasing the amplitude of the signal output from the detection means.

The signal processing means may include selective signal amplifying means, amplitude comparison means (or trigger generation means), and monostable pulse generation means.

The signal processing means may include integrating means to provide an output, the level or magnitude of which will be indicative of the number of solid particles in the fluid. The integrating means may comprise an analog or digital integrator for summing the outputs provided by the shaping means and means for averaging same integral function overtime.

The output means may provide a visual and/or audible indication of the presence of solid particles in the fluid. A visual indication may be provided by one or more light emitters coupled to the pulse generation means and responsive to the output of that means to provide the visual indication. Ideally the or each emitter is coupled to the output of the amplifying means. Where a permanent output record is required, a chart recorder or the like may be used. The recorder may be coupled to receive either the output from the shaping means or the integrating means depending upon what type of visual record is desired. Alternatively, if a dual trace recorder is used, both of these output types may be recorded. An audible output may be provided by coupling a loudspeaker to receive the output from any convenient location. Preferably the speaker is adapted to receive the output from the amplifying means.

The sampling means may be arranged in a flow of fluid caused to pass through the housing. The sampling means is preferably a rotating sampler. Ideally the sampling means comprises a sampling roller mounted for rotation within the housing such that a sample of fluid is picked up by the outer surface of the roller, and as the roller turns, is conveyed to the testing station.

A particular preferred embodiment of a device according to the invention will now be described in relation to the accompanying drawings in which.

Figure 1:
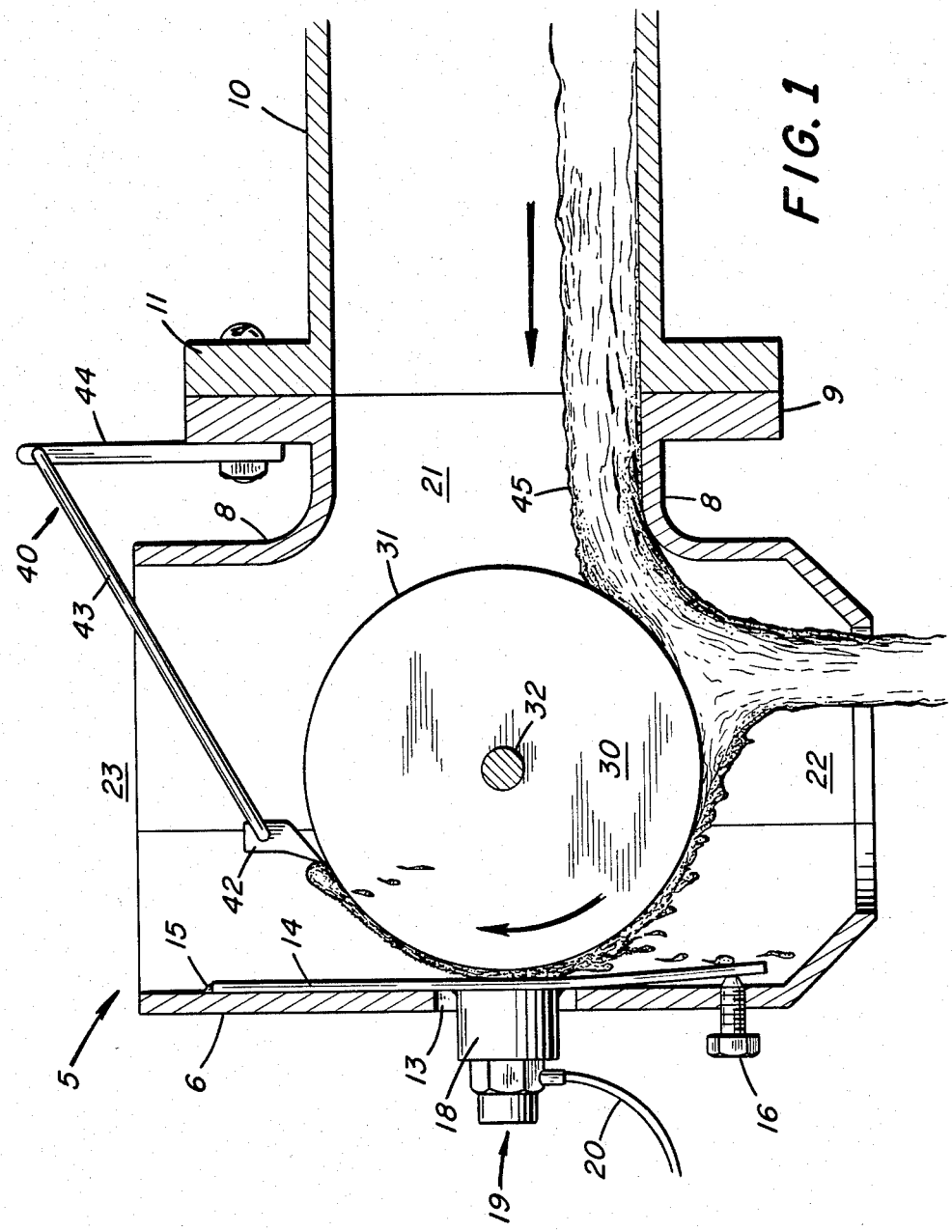
FIG. 1 is a sectional side elevational view of part of the device according to an embodiment of the invention.
Figure 2:
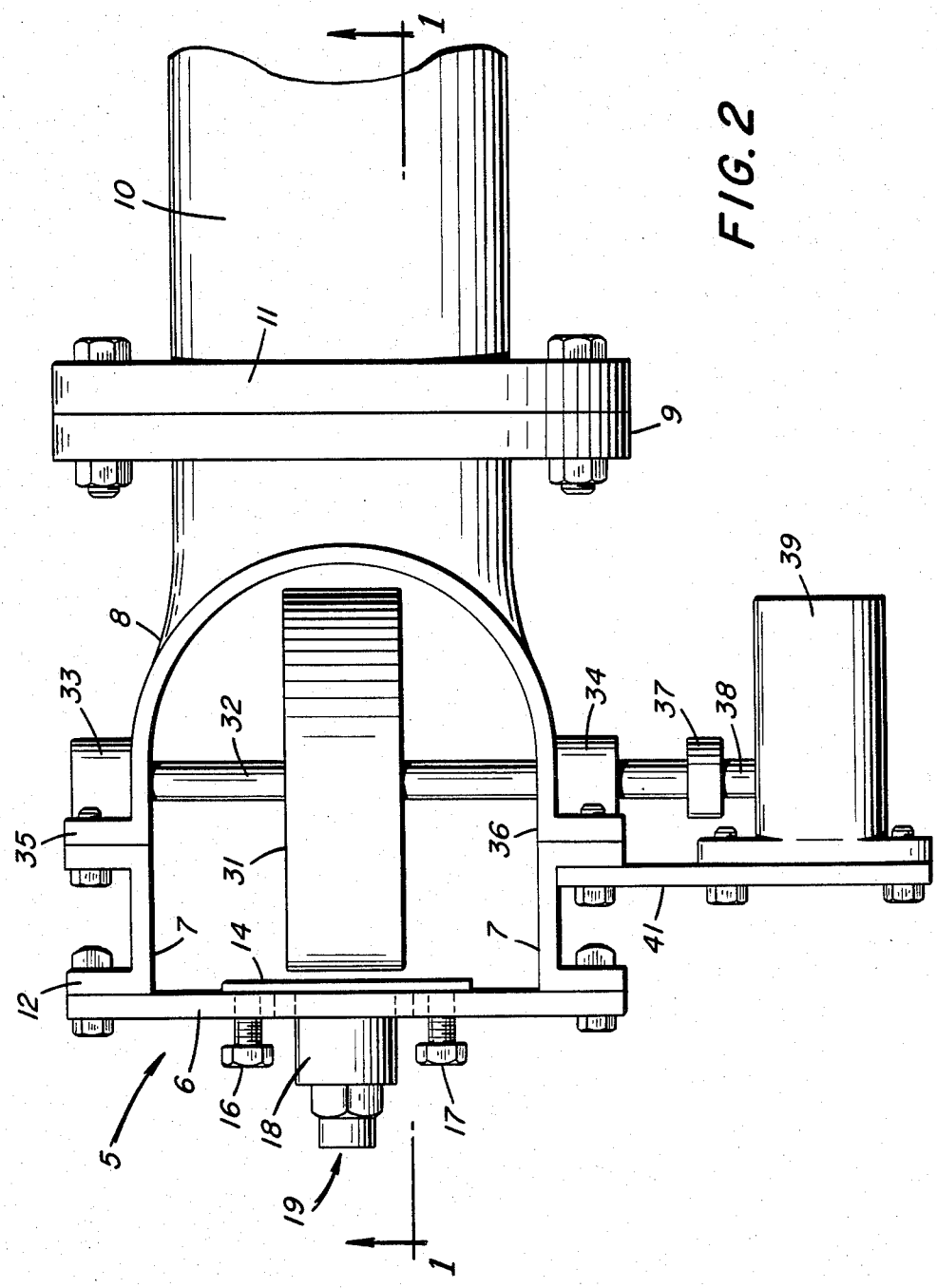
FIG. 2 is a plan elevational view of the device of FIG. 1.

FIGS. 1 and 2 show views of part of the device according to an embodiment of the invention. The device has a housing 5 having a rear wall or backing plate 6 and side walls 7. The side walls 7 have a neck portion 8 and attachment flange 9. Flange 9 enables the housing to be secured to a source of flow of fluid supplied by conduit 10 having a flange 11 similar to flange 9. The rear wall 6 may be integral with the remainder of the housing 5 or may be separate as is evident in FIG. 2. Where wall 6 is separate, flange 12 may be provided on the housing to enable wall 6 to be secured thereto. The flanges may be coupled together in any suitable fashion. For example, bolts may be employed. If desired, a gasket or seal may be positioned between the flanges. The wall 6 has an aperture 13.

Anvil bar 14 is secured to the wall 6 by a weld at 15. The lower end of the bar 14 may be biased away from the wall 6 by bolts 16, 17 screw threaded into the wall. A boss 18 is provided on the bar 14 adjacent the aperture 13. The boss 18 may be formed integral with the bar or subsequently secured thereto. The anvil bar 14 may be made of stainless steel and be about 2 mm thick and 50 mm wide. The boss may be welded or otherwise secured to the bar. An acclerometer may have a threaded stud (not shown) which may be screw threaded into the boss 18. Lead 20 from accelerometer 19 couples the output thereof to signal processing means shown in FIG. 3.

The housing 5 has an inlet 21 for fluid and an outlet 22 through which the fluid may leave the housing. The top 23 of the housing may be closed off by a removable inspection cover. Alternatively the top is left open as shown in FIGS. 1.

Arranged within the housing is a sampling roller 30. Roller 30 is mounted for rotation within housing 5. The sampling roller 30 includes a sample transfer wheel 31 mounted on a shaft 32. The shaft is journalled in bearings 33, 34 located outside housing 5 and secured to abutments 35, 36 respectively. The wheel 31 and bar 14 provide a restricted testing station between them, through which the sample of fluid may pass along a testing path. Any solid particles greater than the space between the bar and the periphery of the wheel 31 are crushed and this causes vibrations which may be detected by the accelerometer 19.

Shaft 32 is connected to a flexible coupling 37 which in turn is connected via a drive shaft 38 to a drive motor 39. Drive motor 39 may include a reduction gear box (not shown). The motor and gear box may be fixed to the housing by a bracket 41.

Once the sample of fluid has travelled past the accelerometer it may be removed from the periphery of the wheel. A scraper 40 having blade 42 which acts against the wheel may be used for this purpose. The blade is secured to a scraper arm 43 which is in turn attached to the housing by bracket 44. The scraper may be biased against the wheel by gravity or by a spring.

A stream of fluid such as molasses, 45 is introduced into the housing through the conduit and a sample of this molasses is picked up by the rotating sampling wheel.

Figure 3:
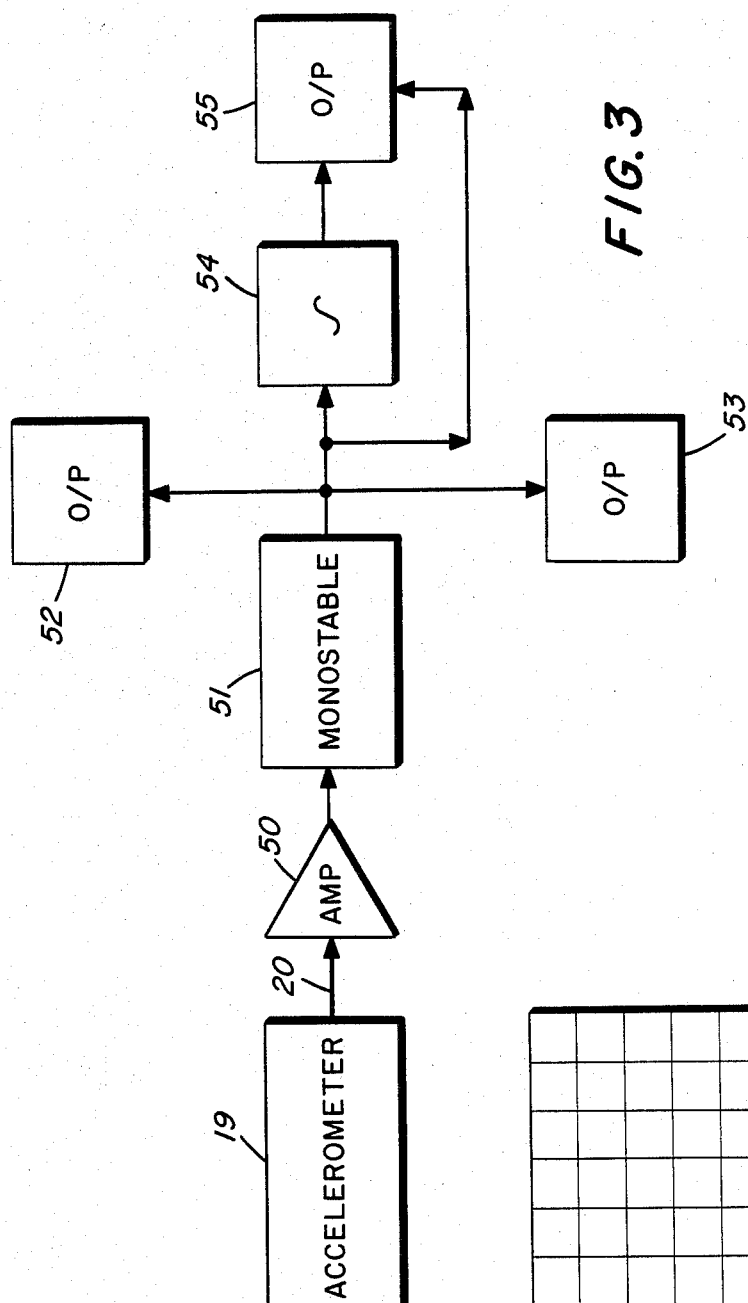
FIG. 3 is a circuit block diagram of signal processing means and output means according to an embodiment of the invention.

FIG. 3 shows a circuit block diagram of a preferred signal processing means and output means according to the invention. Accelerometer 19 has its output coupled via coaxial cable 20 to an amplifier 50. Amplifier 50 may include filtering means to remove unwanted signal components from the accelerometer output. A monostable 51 is coupled to receive the output from the amplifier 50. Monostable 51 further conditions the output derived from the accelerometer 19. Output means 52, 53 may be audible output means, such as a loudspeaker and visible ouput means such as a light. Output means 52, 53 receive the output from monostable 51. Coupled to the output of the monostable is an integrator 54 which sums the number of pulses produced by the monostable. A chart recorder 55 receives both the output from integrator 54 and the output from the monostable. Recorder 55 produces both forms of traces shown in FIG. 4.

OPERATION

The operating principle of the device is shown in FIG. 1. A plain transfer wheel 31 approximately 30 mm wide and 200 mm in diameter rotates slowly, driven by the motor 39. The surface of wheel 31 is partly immersed in the stream of molasses to be tested. A small quantitiy of molasses clings to its surface and is carried to anvil bar which forces out most of the molasses over the ends of the wheel. This molasses then falls back to the main flow. A small adjustable clearance (approximately 0.1 mm) exists between the wheel surface and the anvil bar. A small amount of molasses passes through the gap and is then removed from the roll by the scraper leaving the wheel surface ready to pick up the next sample of molasses. If there are no crystals in the molasses sample, it passes smoothly through the gap. However, if crystals larger than the gap are present, they are crushed between the anvil bar and the wheel surface. As each crystal breaks, faint but clearly detectable shock-waves are created in the anvil. The accelerometer (a vibration sensor) is rigidly attached to the anvil bar and produces electrical signals when vibrations (or shock-waves) are present in the anvil bar. In effect, the instrument collects a sample of molasses, crushes any crystals large enough to be caught against the anvil and produces electrical signals from the resulting crunching noises. The gap between the anvil bar and the wheel enables the very small crystals that are inevitably present in molasses and which are of no concern, to pass undetected.

Figure 5:
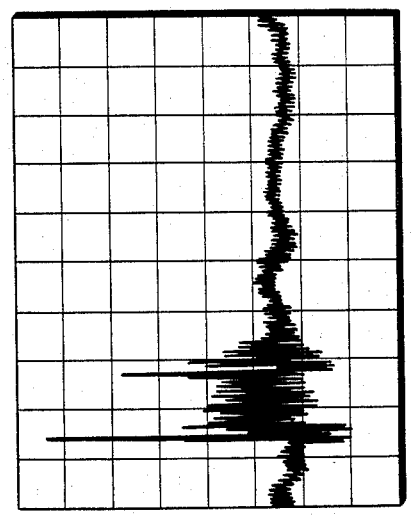
FIG. 5 is an oscillographic record of an amplified signal resulting from the crushing of a solid particle in the fluid.

The shock-waves detected by the accelerometer generate only a very weak electrical signal which has to be greatly amplified. An oscillographic record of the amplified signal resulting from a typical "crunch" is shown in FIG. 5. It consists of a damped oscillation whose main resonant frequency is the natural frequency of the accelerometer's seismic mass. The shock-waves produced by breaking sugar crystals contain some components in the hundreds of thousands of cycles per second as well as in the audible lower frequencies (below 20 kHz). In a sugar mill environment, vibrations in the audio range abound and care must be taken not to allow these to interfere with the "sound" of crunching crystals. Accordingly, the accelerometer should be chosen to have a natural frequency of about 100 kHz (well above the audio range) and unwanted low frequency components can be further reduced by including band pass filters in the amplifying with the amplifying means. One suitable type of accelerometer is the Bruel and Kjaer model 8309 but this is by no means the only one which may be used.

The signal from the breaking up of each crystal is not in a form which can be readily measured or displayed, other than by a skilled operator with a good quality oscilloscope and requires amplification and processing. After amplification, some further signal processing is carried out. Each of the transient bursts of damped oscillation (signifying the breaking of a crystal) is made to trigger the monostable. Thus, for every crystal breaking with an adequately loud "crunch", there results a properly shaped binary pulse of voltage that can be used either to drive a loudspeaker, or to flash an indicator lamp, or as input to an analog or digital integrator. If a loudspeaker is connected, the sound resembles that given off by radiation counters. With no crystals, there is silence, with a few crystals, there are "pops", and if the damage to the screen is large and there are many crystals, the loudspeaker makes a noise resembling a roughly running motor mower at full speed. If an analog time averaging integrator is connected, its output is suitable for plotting on a chart recorder, the trace being near zero for clean molasses, and progressively rising with increasing pulse rates. A digital integrator could display a reading of the average number of crystals per minute (or per hour). Alternatively, the crystal detector's pulse output could be connected to a computer or programmable controller which is configured to log the average pulse rate and set alarms when predetermined levels are exceeded. During factory tests, a simple indicator lamp that flashed for every "crunch" was found very effective. The flashing rate was roughly indicative of the size of the hole in the screen and was easy to interpret.

EXAMPLE

The device of FIGS. 1 and 2 was used to detect solid particles in a molasses flow.

A chart recorder was used to show the signals given by the detection means for various degrees of screen damage. An "event" signal was arranged that would record a short vertical mark on the chart for every pulse from the detector. In addition, an average pulse rate signal was derived by means of analog integrating circuitry, and was recorded on a second chart recorder. The pulse recordings were made at a chart speed of 50 mm/minute, in order that individual pulses might be seen more clearly. The integrator trace did not need such good resolution and it was therefore recorded at a lower speed of 10 mm/minute, thus allowing the illustration to show the instrument's behaviour over a longer period.

Tests were conducted with four different conditions of the screen. The results are shown in FIG. 4. During each test a sample of molasses was collected for crystal analysis, but the analysis subsequently proved to be difficult and was abandoned.

Figures 4A, 4B, 4C, 4D:
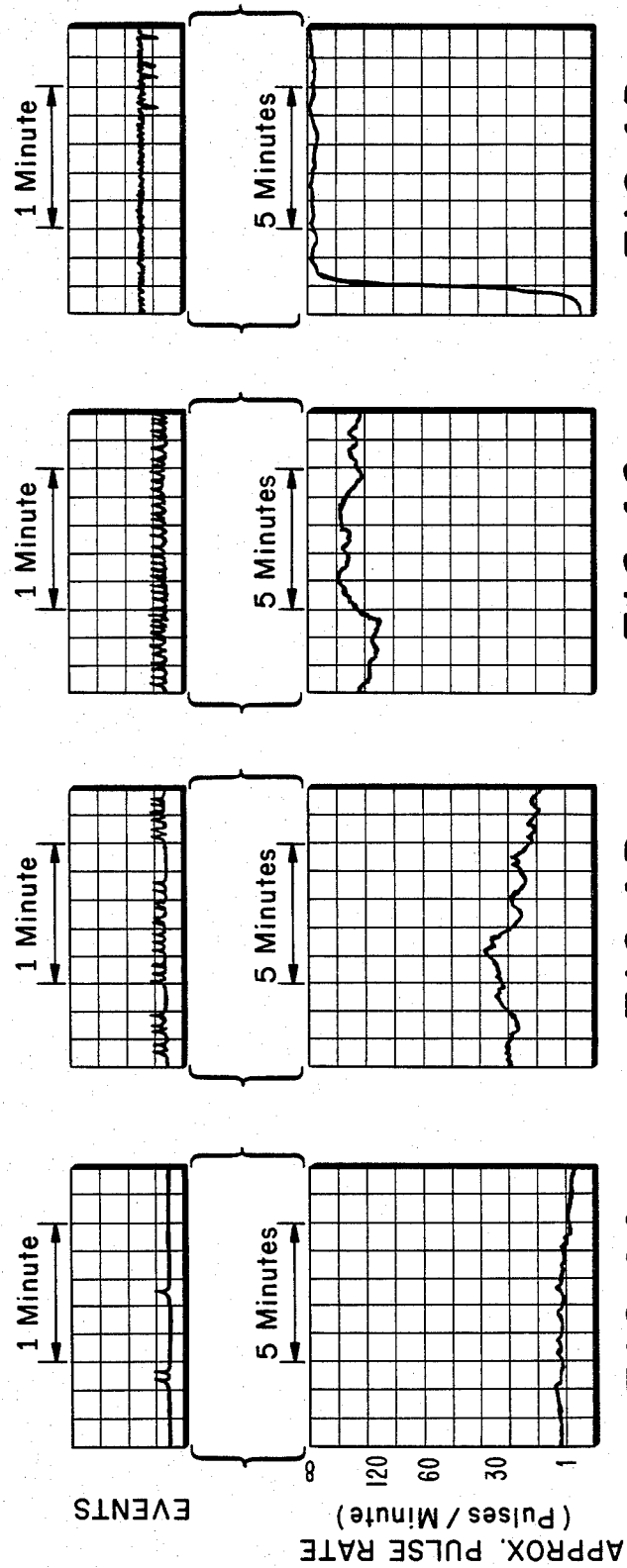
FIGS. 4A, 4B, 4C and 4D are typical outputs from portions of the circuit shown in FIG. 3.

Test 1, the results of which are shown in FIG. 4, was conducted with a virtually undamaged screen. Fourteen count pulses were recorded in this condition over a period of ten minutes (an average of 1.4 per minute), and the recordings of event and integrator signals are shown in FIG. 4A.

Test 11, the results of which are shown in FIG. 4B, was conducted with a 1.6 mm diameter hole drilled approximately half-way up the screen. 250 count pulses were recorded over ten minutes, and the event and integrator traces are shown in FIG. 4B. This condition represents the minimum damage that can typically be detected by spreading a molasses sample on a glass slide and examining against a good light source with the naked eye.

Test 111, the results of which are shown in FIG. 4C, was conducted with a 3.2 mm drill hole in place of the smaller hole of the previous test. 1987 pulses were counted over a 10 minute period and the corresponding chart recordings are shown in FIG. 4C.

Test IV, the results of which are shown in FIG. 4D, was to simulate major damage to the screen. A 10,000 mm$^2$ hole was cut in an already slightly damaged screen. The 10,000 mm$^2$ hole represented a much smaller effective area because some of its was still covered by the overlapping next screen of the centrifugal and the remainder was partly obscured by a basket normally within the centrifugal. The resulting pulse count over ten minutes was 23 678. The chart recordings are shown in FIG. 4D.

Whilst the invention has been described in relation to a device for detecting the presence of solid particles in a fluid, it is also possible to use the device as a viscosity meter. Significant forces occur between the anvil bar and the transfer wheel due to the fluid, such as molasses, being forced through the gap between the bar and the wheel due to in part the shearing of the molasses in the gap. These forces may be converted into useful signals by strain gauges secured to the anvil bar supports and by monitoring motor current and torque. With signal conditioning a viscosity signal could be derived.

It should be appreciated that many changes, modifications or additions may be made to the above described without departing from the spirit or ambit of the invention.

I claim:
1. A device for detecting the presence of solid particles in a fluid including:
 a housing having means defining an inlet for fluid and means defining an outlet for fluid;
 fluid sampling means within the housing, for directing and conveying a sample of the fluid to a testing station within the housing, said testing station having a path defined within it, through which path the fluid sample can flow;
 means for restricting the path through the testing station such that the fluid sample is caused to flow through the testing station and any solid particles in the fluid are crushed or tend to be crushed, thus causing movement or vibrations which may be detected by detection means;
 detection means adjacent the testing station, for detecting said movement or vibrations caused by said crushing; and output means operably coupled to said detection means, for providing a visual and/or audible indication of solid particles in the fluid.

2. A device according to claim 1, wherein said detection means is mounted adjacent an opening in the housing and mounting means.

3. A device according to claim 2, wherein said detection means is an accelerometer and said mounting means is an anvil bar secured to the housing.

4. A device according to claim 3, wherein said sampling means comprises a sampling roller having a sampling wheel mounted on a shaft, said sampling roller being mounted for rotation on said shaft whereby rotation of said roller enables said wheel to transfer fluid from a fluid stream introduced through the inlet to and through the testing station.

5. A device according to claim 4, including drive means for rotating said sampling roller.

6. A device according to claim 4 wherein said anvil bar is movable relative to the sampling roller to enable the spacing between the anvil bar and the wheel to be adjusted.

7. A device according to any claim 1, wherein said output means includes amplifying means coupled to receive the output from said detection means and signal conditioning means to receive the output from said amplifying means whereby the output from said conditioning means is indicative of the presence of solid particles in the fluid.

8. A device according to any claim 1, wherein said output means include amplifying means for receiving the output from said detection means, monostable generator for conditioning the output of the amplifying means, integrator means for summating the output produced by said generator and visual and/or audible output means for providing a visual and/or audible output indicative of the presence of solid particles in the fluid.

9. A device according to claim 4, including a scraper for removing fluid from the periphery of the wheel.

* * * * *